United States Patent
Gururaj et al.

(10) Patent No.: US 10,183,166 B2
(45) Date of Patent: Jan. 22, 2019

(54) SYSTEMS AND METHOD FOR AUTOMATICALLY DETECTING AN MRI ENVIRONMENT FOR PATIENT IMPLANTED WITH MEDICAL DEVICE

(71) Applicant: BOSTON SCIENTIFIC NEUROMODULATION CORPORATION, Valencia, CA (US)

(72) Inventors: Kiran K. Gururaj, Valencia, CA (US); Ross D. Venook, Millbrae, CA (US); Matthew Lee McDonald, Pasadena, CA (US); Joseph M. Bocek, Seattle, WA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 669 days.

(21) Appl. No.: 14/311,059

(22) Filed: Jun. 20, 2014

(65) Prior Publication Data
US 2014/0378820 A1 Dec. 25, 2014

Related U.S. Application Data

(60) Provisional application No. 61/838,187, filed on Jun. 21, 2013.

(51) Int. Cl.
*A61N 1/36* (2006.01)
*A61B 5/055* (2006.01)
(Continued)

(52) U.S. Cl.
CPC .......... *A61N 1/36142* (2013.01); *A61B 5/055* (2013.01); *A61N 1/3718* (2013.01); *A61N 1/3925* (2013.01); *A61B 5/0037* (2013.01)

(58) Field of Classification Search
None
See application file for complete search history.

(56) References Cited

U.S. PATENT DOCUMENTS

| 6,323,649 B1 | 11/2001 | Pace et al. |
| 6,538,443 B2 | 3/2003 | Morich et al. |

(Continued)

OTHER PUBLICATIONS

International Search Report and Written Opinion for PCT Application No. PCT/US2014/043504 dated Oct. 7, 2014.

(Continued)

*Primary Examiner* — Tse Chen
*Assistant Examiner* — Patrick M Mehl
(74) *Attorney, Agent, or Firm* — Lowe Graham Jones PLLC; Bruce E. Black

(57) ABSTRACT

Methods, medical devices, and magnetic resonance imaging (MRI) systems are provided. A patient implanted with a medical device is exposed to a time-varying magnetic field having a signature, thereby inducing mechanical vibrations in at least one component of the medical device. A vibrational characteristic of the mechanical vibrations induced in the component(s) is detected. The vibrational characteristic is analyzed, and the signature of the magnetic field is identified based on the analyzed vibrational characteristic. The medical device is automatically switched from a first operational mode to a second operational mode when the signature is identified.

28 Claims, 10 Drawing Sheets

(51) Int. Cl.
  *A61N 1/39*  (2006.01)
  *A61N 1/37*  (2006.01)
  *A61B 5/00*  (2006.01)

(56) References Cited

U.S. PATENT DOCUMENTS

| | | |
|---|---|---|
| 6,895,280 B2 | 5/2005 | Meadows et al. |
| 7,487,679 B2 * | 2/2009 | Sirrine .................. G01H 1/003 702/39 |
| 7,650,184 B2 | 1/2010 | Walter |
| 8,019,439 B2 | 9/2011 | Kuzma et al. |
| 2006/0173319 A1 * | 8/2006 | Sumi ....................... A61B 8/08 600/437 |
| 2007/0168004 A1 | 7/2007 | Walter |
| 2007/0168007 A1 | 7/2007 | Kuzma et al. |
| 2007/0176596 A1 | 8/2007 | Garcia et al. |
| 2007/0276221 A1 | 11/2007 | Warntjes |
| 2009/0091465 A1 * | 4/2009 | Buckingham ............ A61B 5/11 340/683 |
| 2011/0152667 A1 | 6/2011 | Doerr et al. |
| 2011/0152733 A1 * | 6/2011 | Doerr .................. A61N 1/3718 601/78 |
| 2011/0270338 A1 * | 11/2011 | Cooke .................. A61N 1/3718 607/6 |

OTHER PUBLICATIONS

U.S. Appl. No. 61/612,241, Neurostimulation System for Preventing Magnetically Induced Currents in Electronic Circuitry, Inventor: Gururaj et al., filed Mar. 16, 2012.

U.S. Appl. No. 61/655,938, Neuromodulation System with Default MRI-Mode, Inventor: Rafael et al., filed Jun. 5, 2012.

\* cited by examiner

SYSTEMS AND METHOD FOR AUTOMATICALLY DETECTING AN MRI ENVIRONMENT FOR PATIENT IMPLANTED WITH MEDICAL DEVICE

RELATED APPLICATION DATA

The present application claims the benefit under 35 U.S.C. § 119 to U.S. Provisional Patent Application Ser. No. 61/838,187, filed Jun. 21, 2013. The foregoing application is hereby incorporated by reference into the present application in its entirety.

FIELD OF THE INVENTION

The present inventions relate to medical systems, and more particularly, to MRI-compatible implantable medical devices.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., Arrhythmias). Spinal Cord Modulation (SCM) systems have long been accepted as a therapeutic modality for the treatment of chronic pain syndromes, and the application of tissue stimulation has begun to expand to additional applications such as Angina Pectoralis and Incontinence. Deep Brain Stimulation (DBS) has also been applied therapeutically for well over a decade for the treatment of refractory chronic pain syndromes, and DBS has also recently been applied in additional areas such as movement disorders and Epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems have been applied to restore some functionality to paralyzed extremities in spinal cord injury patients.

Each of these implantable neuromodulation systems typically includes at least one neuromodulation lead implanted at the desired stimulation site and an Implantable Pulse Generator (IPG) implanted remotely from the stimulation site, but coupled either directly to the neuromodulation lead(s), or indirectly to the neuromodulation lead(s) via one or more lead extensions. Thus, electrical pulses can be delivered from the neurostimulator to the electrodes carried by the neuromodulation lead(s) to stimulate or activate a volume of tissue in accordance with a set of stimulation parameters and provide the desired efficacious therapy to the patient. The neuromodulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

IPGs are routinely implanted in patients who are in need of Magnetic Resonance Imaging (MRI). Thus, when designing implantable neuromodulation systems, consideration must be given to the possibility that the patient in which neurostimulator is implanted may be subjected to electromagnetic fields generated by MRI scanners, which may potentially cause damage to patient tissue, malfunction or damage or the neurostimulator, and/or discomfort to the patient.

In MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the presence of a large static magnetic field. Present-day MRI scanners can have maximum gradient strengths of 100 mT/m, and rapid switching times that yield slew rates at or exceeding 200 mT/m/ms, which is capable of generating unintended peripheral nerve stimulation in patients even without the presence of an implantable device. Typical MRI scanners create gradient fields in the range of 1 Hz to 10 KHz, and radio frequency (RF) fields of 64 MHz for a 1.5 Tesla scanner and 128 MHz for a 3 Tesla scanner. Both of these types of applied fields are activated in bursts, which have comparable frequencies to stimulation therapy frequencies.

While conventional IPGs implanted within a patient undergoing an MRI may be reprogrammed or deactivated (e.g., using a clinician programmer) to temporarily shut down for the duration of the MRI, newer versions of IPGs may be switched to an MRI-specific mode that enables a limited functioning of the implanted system during the MRI. In one technique, the stimulation circuitry of the IPG is deactivated, while allowing the IPG to communicate with the RC. In one novel technique described in U.S. Provisional Patent Application Ser. No. 61/612,241, entitled "Neuromodulation System for Preventing Magnetically Induced Currents in Electronic Circuitry," which is expressly incorporated herein by reference, voltage supply rails of the IPG electronics are increased to prevent electrical energy induced on the stimulation leads by the MRI fields from circulating through the IPG that may otherwise cause damage to the IPG electronics or painful or unintended stimulation to the patient. To make use of this option, the IPG may be manually placed into the MRI-specific mode before undergoing the MRI procedure.

However, the patient or medical personnel may forget to place the IPG in the MRI-specific mode or otherwise deactivate the IPG before the MRI procedure. The patient may not be mentally conscious, in some cases, and therefore may be unable to inform the medical personnel to manually place the IPG in the MRI-specific mode or otherwise deactivate the IPG. By failing to place the IPG in the MRI-specific mode or otherwise deactivate the IPG, the patient may be put at risk of being exposed to unwanted electrical stimulation and/or discomfort or the IPG may be put at risk of damage during the MRI procedure.

There, thus, remains a need to automatically deactivate or place the IPG in the MRI-specific mode without requiring user intervention. Additionally, since MRI-specific modes are, in general, not identical to modes that deliver optimal therapy, it is also valuable that the method of automatically entering an MRI-specific mode have high sensitivity and specificity for MRI.

SUMMARY OF THE INVENTION

In accordance with a first aspect of the present inventions, a method of automatically identifying a signature in a time-varying magnetic field generated by a magnetic resonance imaging (MRI) device is provided. The signature may be, e.g., a variance in a magnitude, a frequency, and/or a duty cycle of the magnetic field. The method comprises exposing a patient to the magnetic field, thereby inducing mechanical vibrations in at least one component of a medical device (e.g., a case, printed circuit board, and/or battery) implanted in the patient. The mechanical vibrations may be linear in nature and/or torsional in nature. If the medical device is an implantable pulse generator, the magnetic field preferably has an amplitude that does not cause the implantable pulse generator to inadvertently stimulate the patient in a harmful manner.

The method further comprises detecting a vibrational characteristic of the mechanical vibrations induced in the component(s). If the signature is a variance in the magnitude of the magnetic field, the vibrational characteristic may be a magnitude of the induced mechanical vibrations. If the signature is a variance in the frequency of the magnetic field, the vibrational characteristic may be a frequency of the induced mechanical vibrations. If the signature is a variance in a duty cycle of the magnetic field, the vibrational characteristic may be a duty cycle of the induced mechanical vibrations. In one embodiment, the vibrational characteristic is a common characteristic of the component(s). In another embodiment, the vibrational characteristic is a differential characteristic of the component(s). In this case, if the component is a single component, the differential vibrational characteristic may be detected between at least two different surfaces of the single component. If the component(s) comprises at least two different components (e.g., a case or printed circuit board and a battery), the differential vibrational characteristic may be detected between the different components. The vibrational characteristic may be detected by measuring, e.g., a vibrational acceleration of the component(s), a vibrational strain of the component(s), and/or a vibrational displacement of the component(s). The vibrational characteristic may be detected in one dimension or multiple dimensions.

The method comprises analyzing the vibrational characteristic, and identifying the signature of the magnetic field based on the analyzed vibrational characteristic. The analysis of the vibrational characteristic may, e.g., comprise identifying a pattern in the vibrational characteristic corresponding to a pattern in the magnetic field or thresholding the vibrational characteristic. The vibrational characteristic may be analyzed in a time-domain or a frequency domain.

The method may further comprise automatically switching the medical device from a first operational mode to a second operational mode when the signature is identified. In this case, the method may further comprise exposing the patient to an additional time-varying magnetic field having another signature (which may be different from the first signature), thereby inducing additional mechanical vibrations in the component(s), detecting an additional vibrational characteristic of the additional induced mechanical vibrations in the component(s), analyzing the additional vibrational characteristic, identifying the other signature of the magnetic field based on the analyzed other vibrational characteristic, and automatically switching the medical device from the second operational mode to the first operational mode when the signature is identified. Alternatively, the medical device may be automatically switched from the second operational mode to the first operational mode when a predetermined period has elapsed.

The method may further comprise performing an MRI scan on the patient when the medical device is in the second operational mode, thereby generating an MRI of the patient. In this case, the first operational mode may be a fully operational mode, and the second operational mode may be an MRI-specific mode. In this case, the patient may be exposed to the magnetic field during an MRI pre-scan on the patient, and in this case where an additional magnetic field is generated, may be exposed to it during an MRI post-scan of the patient.

In accordance with a second aspect of the present inventions, a medical device configured for being implanted in a patient is provided. The medical device comprises at least one component configured for mechanically vibrating when exposed to a time-varying magnetic field having a signature (e.g., a variance in a magnitude, a frequency, and/or a duty cycle of the magnetic field). The mechanical vibrations may be linear in nature and/or torsional in nature.

The medical device further comprises a sensing device (e.g., an accelerometer, strain gauge, etc.) configured for detecting a vibrational characteristic of the mechanical vibrations in the component(s) (e.g., a case, printed circuit board, and/or battery). In one embodiment, the component(s) comprises the sensing device. If the signature is a variance in the magnitude of the magnetic field, the vibrational characteristic may be a magnitude of the induced mechanical vibrations. If the signature is a variance in the frequency of the magnetic field, the vibrational characteristic may be a frequency of the induced mechanical vibrations. If the signature is a variance in a duty cycle of the magnetic field, the vibrational characteristic may be a duty cycle of the induced mechanical vibrations.

The medical device further comprises control circuitry configured for analyzing the vibrational characteristic and identifying the signature of the magnetic gradient field based on the analyzed vibrational characteristic. The control circuitry may, e.g., be configured for analyzing the vibrational characteristic and for identifying a pattern in the vibrational characteristic that corresponds to a pattern in the magnetic gradient field or analyzing the vibrational characteristic by thresholding the vibrational characteristic. The control circuitry may be configured for analyzing the vibrational characteristic in a time-domain and/or a frequency domain. In one embodiment, the vibrational characteristic is a common characteristic of the component(s). In another embodiment, the vibrational characteristic is a differential characteristic of the component(s). In this case, the component(s) may be a single component, and the control circuitry may be configured for detecting the differential vibrational characteristic between at least two different surfaces of the single component. Or, the component(s) may comprise at least two different components (e.g., a case or printed circuit board and a battery).

The control circuitry may further be configured for automatically switching the medical device from a first operational mode (e.g., a fully functioning mode) to a second operational mode (an MRI-specific mode) when the signature is identified. In this case, the component(s) may be further configured for mechanically vibrating when exposed to an additional time-varying magnetic field having another signature (which may be different from the first signature), the sensing device may be further configured for detecting an additional vibrational characteristic of the additional induced mechanical vibrations in the component(s), and the control circuitry may be further configured for analyzing the additional vibrational characteristic, identifying the other signature of the magnetic field based on the analyzed other vibrational characteristic, and automatically switching the medical device from the second operational mode to the first operational mode when the signature is identified. Alternatively, the control circuitry may be configured for automatically switching the medical device from the second operational mode to the first operational mode when a predetermined period has elapsed.

In accordance with a third aspect of the present inventions, a magnetic resonant imaging (MRI) system is provided. The MRI system comprises memory configured for storing a signature, magnetic coils configured for transmitting a time-varying magnetic field to a patient implanted with a medical device, such that mechanical vibrations are induced in the medical device, and a controller configured for encoding the magnetic field with the signature, such that the mechanical vibrations induced in the medical device contain the signature (e.g., by varying the magnitude, frequency, and/or pulse duty of the magnetic field). In one embodiment, the magnetic field is associated with an MRI pre-scan. The memory may optionally be configured for storing another signature (which may be different from the first signature), the magnetic coils may be configured for transmitting an additional time-varying magnetic field to the patient, such that additional mechanical vibrations are induced in medical device, and the controller may be configured for encoding the additional magnetic field with the other signature, such that the additional mechanical vibrations that are induced in the medical device contain the other signature. In one embodiment, the additional magnetic field is associated with an MRI post-scan. If the medical device is an implantable pulse generator, the magnetic coils are preferably configured for generating the magnetic gradient field with an amplitude that does not cause the implantable pulse generator to inadvertently stimulate the patient.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to MRI-compatible neuromodulation systems, in particular spinal cord modulation (SCM) systems. However, it is to be understood that the while the invention lends itself well to applications in SCM, the invention, in its broadest aspects, may not be so limited. Rather, the invention may be used with any type of implantable medical device. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
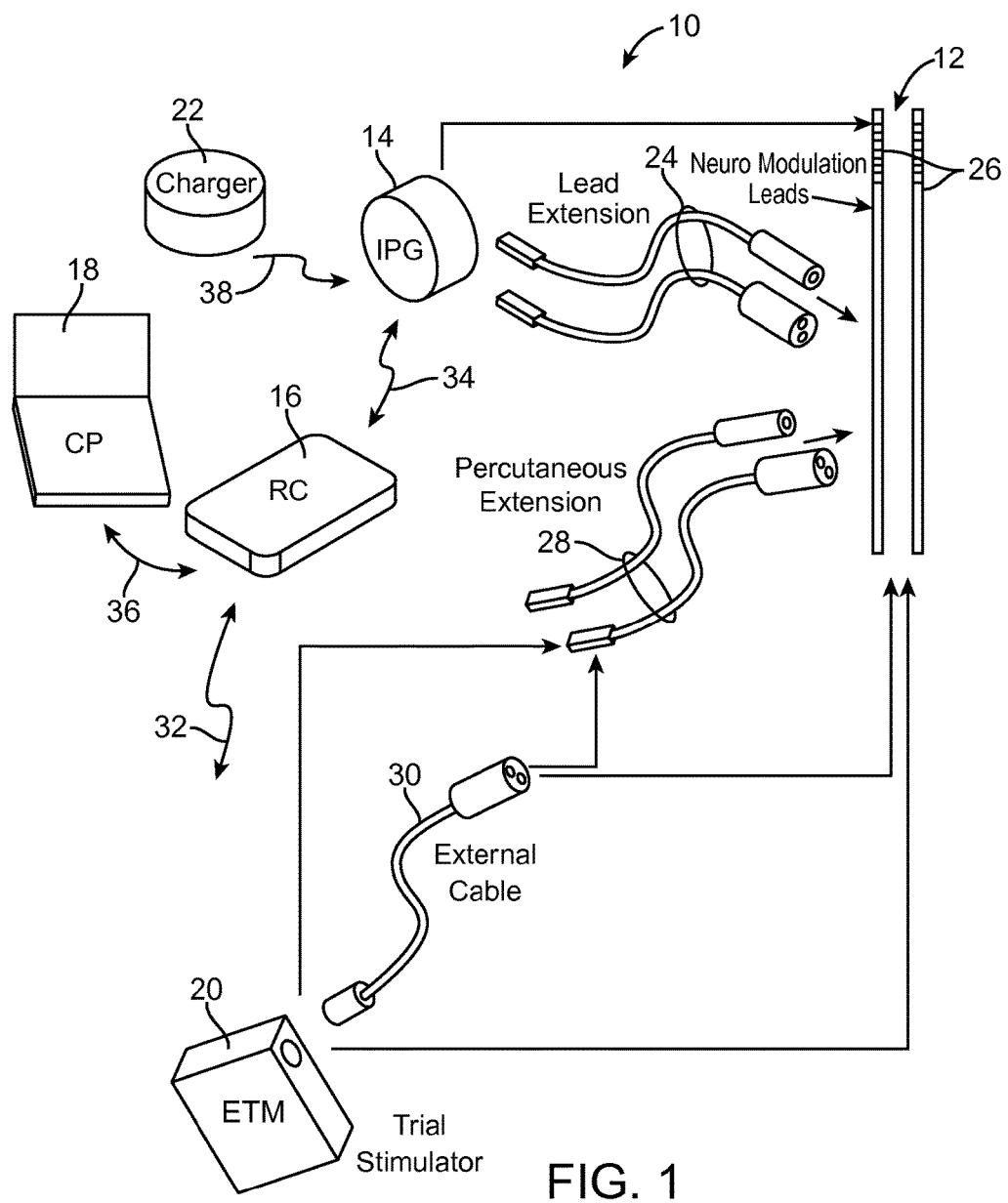
FIG. 1 is a plan view of a Spinal Cord Modulation (SCM) system constructed in accordance with one embodiment of the present inventions.

Turning first to FIG. 1, an exemplary neuromodulation system, SCM system 10, generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation energy delivered to the patient. Thus, any functions described herein with respect to the IPG 14 can likewise be performed with respect to the ETM 20.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the CP 18, ETM 20, and external charger 22 will not be described herein. Details of exemplary embodiments of these devices are disclosed in U.S. Pat. No. 6,895,280, which is expressly incorporated herein by reference.

Figure 2:
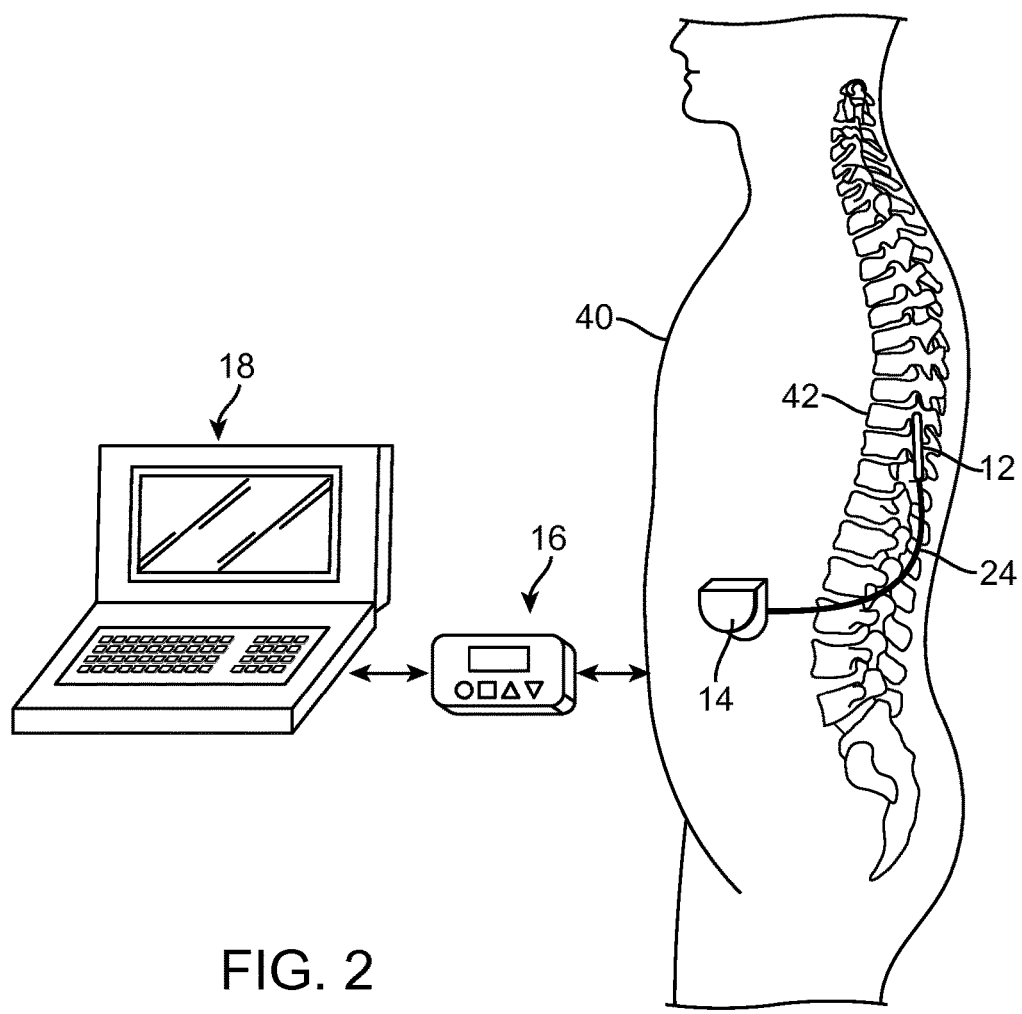
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

Figure 3:
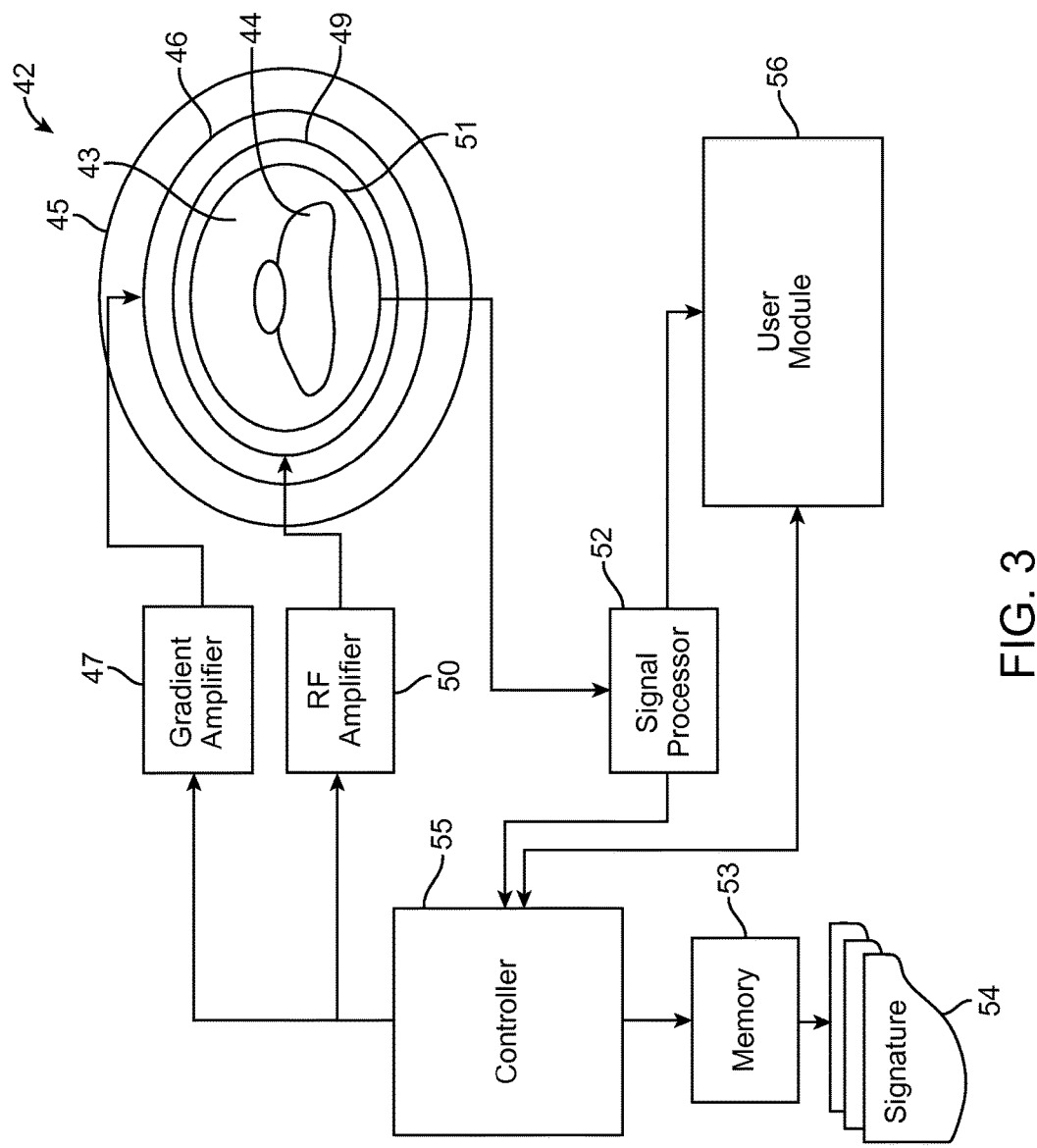
FIG. 3 is a block diagram of the internal components of a Magnetic Resonant Imaging (MRI) system used to perform an MRI scan on the patient of FIG. 2 implanted with the SCM system of FIG. 1.

Significant to the present inventions, when the patient is undergoing a Magnetic Resonant Imagining (MRI) scan, the IPG 14 is configured to automatically switch from a normal mode to an MRI-specific mode when the IPG 14 detects a signature in the magnetic gradient field generated by a MRI system 42 (shown in FIG. 3). Optionally, the IPG 14 is configured to automatically switch from the MRI-specific mode to the normal mode when the IPG again detects a different signature in the magnetic gradient field generated by the MRI system 42. In alternative embodiments, rather than automatically switching the IPG 14 from the normal mode to the MRI-specific mode, a notification message may be provided to the user via the RC 16 or CP 18 upon detection of the signature to prompt the user to switch the IPG 14 to the MRI-specific mode from the normal mode if the IPG 14 has not already been switched to the MRI-specific mode. In a similar manner, a notification message may be provided to the user via the user via the RC 16 or CP 18 upon detection of the different signature to prompt the user to switch the IPG 14 to the normal mode from the MRI-specific mode. Although the embodiment described herein incorporates the signature within the magnetic gradient field, it should be appreciated that the signature may be incorporated into any time-varying magnetic field generated by the MRI system 42, such as static magnetic field shimming coils.

In the illustrated embodiment, when in MRI-specific mode, the IPG 14 may take one of a variety of actions that prevent, or at least minimizes, the potentially harmful effects that include inadvertent stimulation of the patient and damage to the IPG electronics, caused by the combination of static and gradient magnetic fields and radio frequency (RF) fields generated during the MRI scan, as well as preventing the magnetic field generated during the MRI scan from shutting down the IPG 14.

In one novel technique described in U.S. Provisional Patent Application Ser. No. 61/612,241, entitled "Neurostimulation System for Preventing Magnetically Induced Currents in Electronic Circuitry," which is expressly incorporated herein by reference, the IPG 14, in response to a control signal from the RC 16 or CP 18, is placed into an MRI-specific mode by increasing the voltage supply rails of the IPG electronics to prevent the current induced on the leads from entering the IPG electronics, while preventing the IPG 14 from being inadvertently shut down by the MRI scan, thereby allowing the IPG 14 to continue to prevent the entry of the induced electrical current as well as to continue to monitor the magnetic field generated by the MRI, e.g., to determine when the MRI scan has been initiated and/or terminated. Other functions include shorting the induced current to ground or the case, or adding high impedance within the leads or between the leads and the IPG electrodes, as described in U.S. Provisional Patent Application Ser. No. 61/655,938, entitled "Neurostimulation System with Default MRI-specific mode," which is expressly incorporated herein by reference. When in MRI-specific mode, the modulation output circuitry (described in further detail below) may be deactivated, but the IPG 14 may be allowed to communicate with the RC 16. Preferably, when in the MRI-specific mode, the IPG 14 is prevented from generating and outputting electrical stimulation energy to the neuromodulation leads 12 until switched back to the normal mode.

To eliminate false positives, the IPG 14 is configured to only switch to the MRI-specific mode when triggered by a sensed signature encoded within the magnetic gradient field. The signature of the magnetic gradient field is a pattern in the magnetic gradient field, which may be achieved in a number of ways; for example, by varying a magnitude, frequency, and/or duty cycle of the magnetic gradient field, as will be described in further detail below.

The signature of the magnetic gradient field may be programmable by a technician or a manufacturer of the MRI system 42. For example, the technician or manufacturer may devise a special signature for an MRI pre-scan to enable the IPG 14 to identify the signature and switch to the MRI-specific mode. The MRI pre-scan may last just a few seconds, in one example, to prompt the IPG 14 to switch to the MRI-specific mode. Once the IPG 14 is in MRI-specific mode, the patient may safely undergo the MRI procedure without the risk of hurting the patient and/or causing damage to the IPG 14. Similarly, the technician or the manufacturer may also devise another signature for an MRI post-scan to enable the implanted medical device to identify the other signature and switch out of the MRI-specific mode. The MRI post-scan prompts the IPG 14 to automatically switch back to the normal mode from the MRI-specific mode, thereby allowing for a resumption of tissue modulation without undue delay. Preferably, the signature of the MRI pre-scan is different from that of the MRI post-scan, which enables the IPG 14 to switch to the right mode based on the identity of the signature of the magnetic gradient field. In an alternate embodiment, the IPG 14 may automatically switch back to the normal mode from the MRI-specific mode after a predetermined time period has elapsed (e.g., the IPG 14 may be programmed such that the IPG 14 automatically switches back to the normal mode from the MRI-specific mode after a period of 2 hours has elapsed). Although the present application will focus on signatures that enable the IPG 14 to switch in and out of the MRI-specific mode, it should be appreciated that other signatures of the magnetic gradient field may also be detected and identified by the IPG 14 to be used in other applications.

Turning now to FIG. 3, the main internal features of the MRI system 42 will be briefly described. The MRI system 42 includes a cylindrical bore 43 in which the magnetic gradient field is ultimately generated when a patient 44 undergoes an MRI scan.

The MRI system 42 (the cross-section of which is shown for illustrative purposes in FIG. 3) comprises a main magnet 45 configured for generating a static magnet field in the cylindrical bore 43. The main magnet 45 is driven by a static magnet power supply, and may be a resistive main magnet or a superconducting main magnet. Although the MRI system is preferably a closed bore-type MRI system, it should be appreciated that open magnet systems and/or other known types of MRI scanners may also be used.

The MRI system 42 further comprises gradient coils 46 configured for producing time-varying magnetic field gradients in the magnetic field produced by the main magnet 45. The gradient coils 46 create gradients along x, y and z axes and are applied for slice selection and spatial encoding of the magnetic field. The MRI system 42 further comprises gradient amplifiers 47 that apply current pulses to the gradient coils 46 in order to create the gradients.

The MRI system 42 further comprises Radiofrequency (RF) transmitter coils 49 configured for generating RF pulses to rotate the magnetic gradient field. The MRI system 42 also comprise RF amplifiers 50 that apply current pulses to the RF transmitter coils 46. The MRI system 42 also comprises RF receiver coils 51 configured for detecting precessing magnetization of the hydrogen nuclei in the patient 44, and converting the precessing magnetization into electrical signals. A signal processor 52 receives the electrical signals from the RF receiver coils 51 and generates images based on the electrical signals. The MRI system 42 comprises memory 53 configured for storing a set of signatures 54. Each signature 54 dictates the pattern of the magnetic gradient field ultimately generated by the MRI system 42.

The MRI system 42 further comprises a controller 55 configured for operating the gradient pulse amplifiers 47 and RF amplifiers 50 by sending instructions, commands and/or requests to generate gradients and RF pulses respectively. The controller 55 is also configured for encoding the magnetic gradient field with a signature 54, stored in the memory 53. In some cases, the signature 54 may be selected by the user through the user module. In other cases, the controller 55 may be configured to automatically select a signature associated with an MRI pre-scan before an MRI scan, and another signature associated with an MRI post-scan after the MRI scan. The controller 55, for example, may be a computer with a control interface and a data interface. The controller 55 may also analyze the data received from the signal processor 52 and reconstruct the images from the MRI scan.

The MRI system 42 also includes a user module 56 that provides a means for the user (e.g., technician) to communicate with the MRI system 42. To this end, the user module 56 is configured for receiving user input through a keyboard (or any other input device), a control panel and/or a display. The user may be able to program a set of variables related to the MRI scan (e.g., duration of the scan, parameters of the magnetic gradient field, etc.), and enter relevant information (e.g., patient information, etc.) into the MRI system 42 through the user module 56. Similarly, the user may also program signatures of the magnetic gradient field for MRI pre-scans or MRI post-scans through the user module 56, as mentioned above.

The components of the MRI system 42 communicate with each other via electrical and/or data connections. Data connections may occur through direct wired links, fiber optic connections and/or wireless communication links. Further details describing the components of the MRI system 42 are disclosed in U.S. Pat. No. 6,538,443, entitled "MRI gradient coil with variable field of view and apparatus and methods employing the same," and U.S. Pat. No. 6,323,649, entitled "Modular MRI gradient amplifier using unipolar PWM drive," the disclosures of which are expressly incorporated herein by reference.

Figure 4:
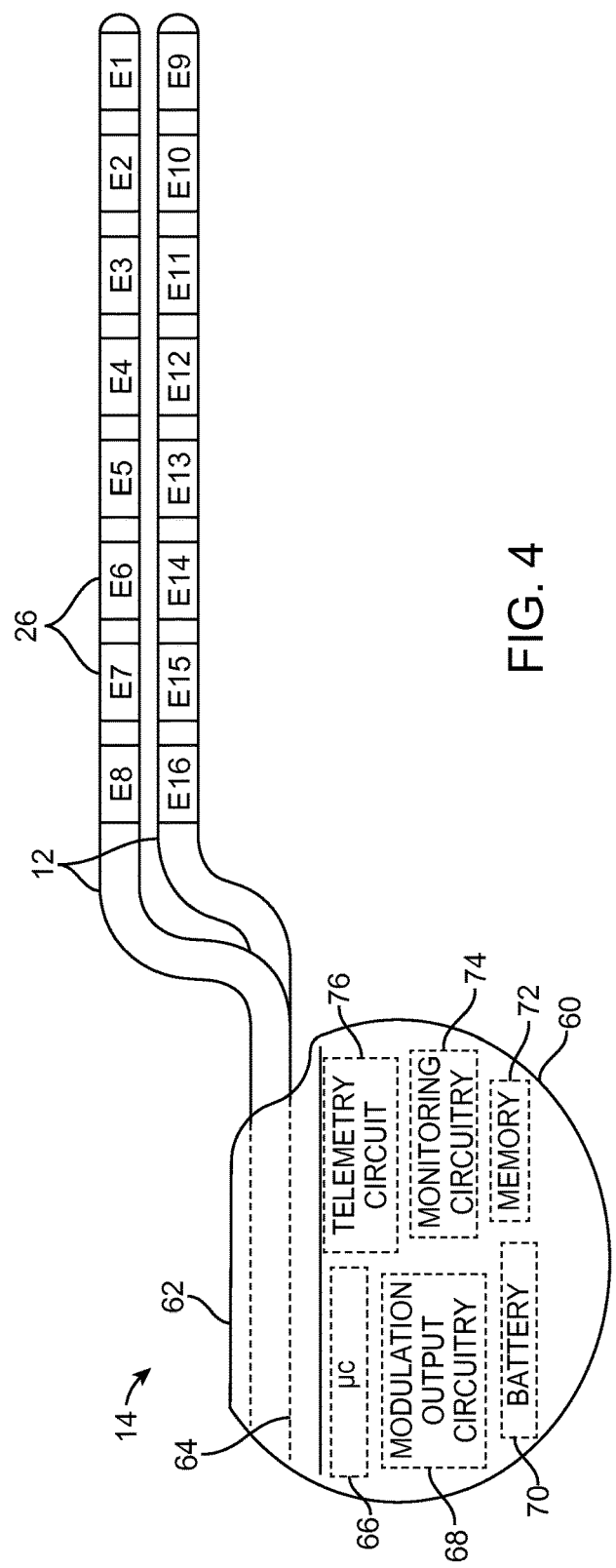
FIG. 4 is a plan view of an implantable pulse generator (IPG) and two percutaneous leads used in the SCM system of FIG. 1.

Referring now to FIG. 4, the external features of the neuromodulation leads 12 and the internal components of the IPG 14 will be briefly described. Each of the neuromodulation leads 12 has eight electrodes 26 (respectively labeled E1-E8 and E9-E16). The actual number and shape of leads and electrodes will, of course, vary according to the intended application. Further details describing the construction and method of manufacturing percutaneous neuromodulation leads are disclosed in U.S. patent application Ser. No. 11/689,918, entitled "Lead Assembly and Method of Making Same," and U.S. patent application Ser. No. 11/565,547, entitled "Cylindrical Multi-Contact Stimulation lead for Neural Stimulation and Method of Making Same," the disclosures of which are expressly incorporated herein by reference.

The IPG 14 comprises an outer case 60 for case the electronic and other components (described in further detail below). The outer case 60 is composed of an electrically conductive, biocompatible material, such as titanium, and forms a hermetically sealed compartment wherein the internal electronics are protected from the body tissue and fluids. In some cases, the outer case 60 may serve as an electrode. The IPG 14 further comprises a connector 62 to which the proximal ends of the stimulation leads 12 mate in a manner that electrically couples the electrodes 26 to the internal electronics (described in further detail below) within the outer case 60. To this end, the connector 62 includes one or more ports for receiving the proximal end(s) of the neuromodulation lead(s) 12. In the case where the lead extensions 24 are used, the port(s) 64 may instead receive the proximal ends of such lead extensions 24.

The IPG 14 further comprises interior electronic circuitry, such as a microcontroller 66, a modulation output circuitry 68, a battery 70, a memory 72, a monitoring circuitry 74, a telemetry circuitry 76, and other suitable components known to those skilled in the art. The monitoring circuitry 74 is configured for measuring electrical parameter data (e.g., electrode impedance and/or electrode field potential) from the electrodes 26. Significantly, the monitoring circuitry 74 is also configured for monitoring one or more vibrational characteristics (e.g., amplitude, frequency, and/or duty cycle) of mechanical vibrations induced within one or more components of the IPG 14 when exposed to a magnetic gradient field generated by the MRI system 42. As will be described in further detail below, one or more sensing devices may be located on selected IPG components for sensing the mechanical vibrations in the IPG component(s).

The microcontroller 66 executes a suitable program stored in the memory 72 for directing and controlling the electrical stimulation therapy performed by IPG 14, as well as analyzing the vibrational characteristic(s) obtained from the monitoring circuitry 74, identifying the signature encoded within the magnetic gradient field based on the analyzed vibrational characteristic(s), and automatically switching the IPG from the normal mode to the MRI-specific mode, or optionally from the MRI-specific mode to the normal mode, upon identifying that signature. The telemetry circuitry 76 (including an antenna) is configured for receiving programming data (e.g., the operating program and/or neurostimulation parameters) from the RC 16 in an appropriate modulated carrier signal, and demodulating the carrier signal to recover the programming data, which programming data is then stored in memory 72. The battery 70, which may be a rechargeable lithium-ion or lithium-ion polymer battery, provides operating power to IPG 14.

Figure 5:
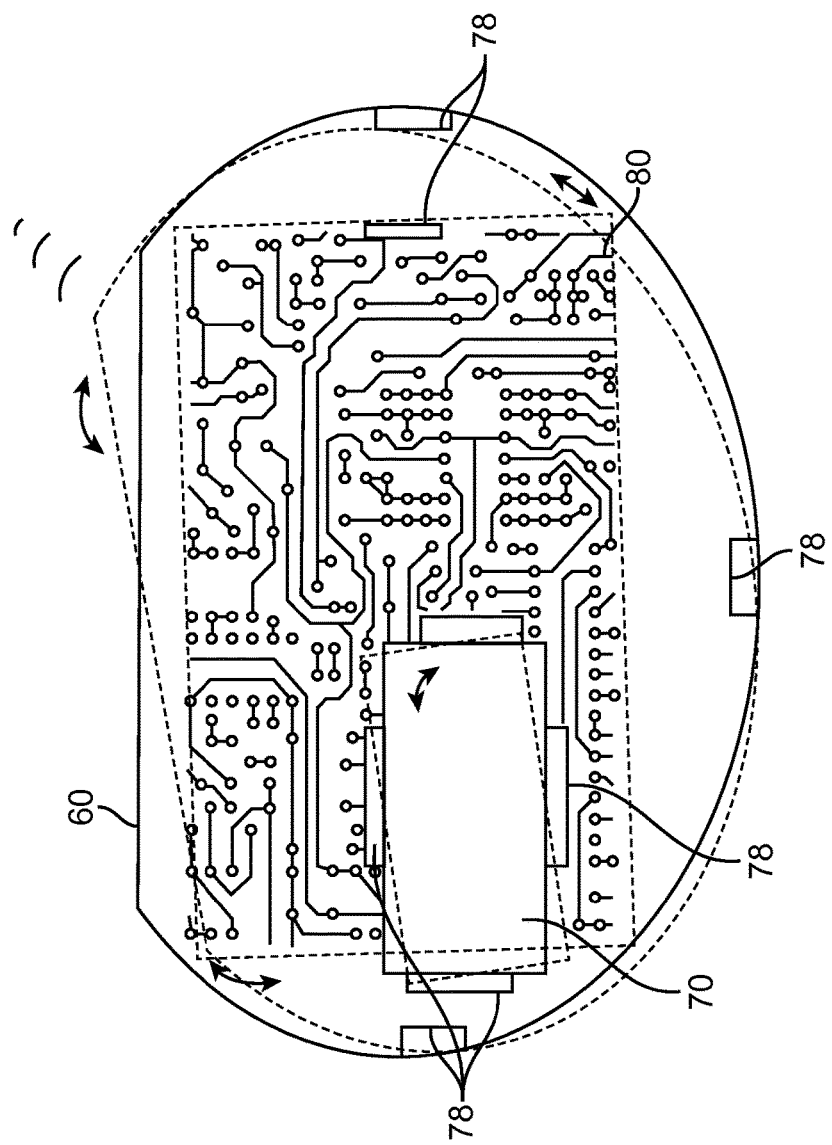
FIG. 5 is a plan view of the main components of the IPG of FIG. 4 that are configured to vibrate.

As described above, sensing devices may be located in various locations in the IPG 14 in order to sense mechanical vibrations of certain components that may vibrate when exposed to a magnetic gradient field generated by the MRI system 42. For example, with reference to FIG. 5, sensing devices 78 are located on various components of the IPG 14, which are configured to vibrate when exposed to a magnetic gradient field. Preferably, the surfaces on which the sensing devices 78 are located are selected to allow eddy currents to flow in response to being exposed to the magnetic field, but vibrate at a safe level for the patient without causing damage to the IPG 14. Control of vibrational forces can be accomplished by controlling the dimensions, sheet resistivity, and mass, rotational inertia, and mechanical damping of the element configured to vibrate (see ISO TS 10974, Clause 12).

In the illustrated embodiment, the sensing devices 78 are mounted to the IPG case 60, the battery 70, and a printed circuit board (PCB) 80 on which the battery 70 and the other electronic components are mounted. While all the components of the IPG 14 may vibrate, the present application will focus on the mechanical vibrations of the IPG case 60, battery 70, and the printed circuit board (PCB) 80. In alternative embodiments, the sensing devices 78 may be mounted on only one component. When the IPG 14 is exposed to the magnetic gradient field, the component(s) of the IPG 14 vibrate, and the sensing devices 78 detect the mechanical vibrations of the case 60, the battery 70, and the PCB 80. Alternatively, the sensing devices 78, themselves, can be made to vibrate in response to the magnetic gradient field irrespective of the vibration of the surface on which they are located.

It should be appreciated that vibrations induced within the component by the time varying magnetic field may be both linear in nature and torsional in nature. As such, the sensing devices 78 can be selected and arranged to measure the vibrational characteristic(s) as a function of linear vibration and/or torsional vibration. In one embodiment, because torsional vibration of a component, as opposed to linear vibration of a component, is more apt to carry a signature of the MRI-induced vibration that is more easily distinguishable from other environmental factors (i.e., a signature of MRI induced vibrations is that of a torque induced in a conductive sheet, as opposed to primarily translational vibrations that can be induced from other environmental sources), the sensing devices 78 can be selected and arranged in a manner that detects torsional vibration in a component in order to provide better specificity in detecting MRI-induced vibrations. For example, a plurality of sensing devices 78 can be placed around the edge of a conductive sheet that forms a component or a portion thereof.

The sensing devices 78 detect, over time, the vibrational characteristics (e.g., amplitude, frequency, and/or duty cycle) associated with the mechanical vibrations of the IPG 14. Since the signature of the magnetic gradient field is a pattern in the magnetic gradient field (which may be achieved by varying a magnitude, frequency, and/or duty cycle of the magnetic gradient field as described above), a variance in the magnetic gradient field corresponds to a variance in the mechanical vibrations of the component(s) of the IPG 14. Therefore, when there is a variance in the magnitude of the magnetic gradient field, the vibrational characteristic that is detected and analyzed is a magnitude of the induced mechanical vibrations of the component(s). Similarly, when there is a variance in the frequency of the magnetic gradient field, the vibrational characteristic that is detected and analyzed is a frequency of the induced mechanical vibrations of the component(s). Therefore, when there is a variance in the frequency of the magnetic gradient field, the vibrational characteristic that is detected and analyzed is a frequency of the induced mechanical vibrations of the component(s). And when there is a variance in the duty cycle of the magnetic gradient field, the vibrational characteristic that is detected and analyzed is a duty cycle of the induced mechanical vibrations of the component(s). Therefore, when there is a variance in the duty cycle of the magnetic gradient field, the vibrational characteristic that is detected and analyzed is a duty cycle of the induced mechanical vibrations of the component(s).

Figure 6A:
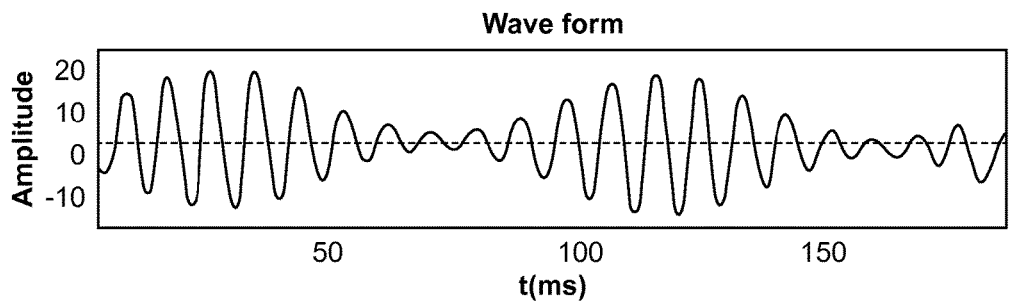
FIG. 6a is a timing diagram of a vibrational waveform measured by the IPG of FIG. 4 when the amplitude of a magnetic gradient field generated by the MRI system of FIG. 3 is varied.
Figure 6B:
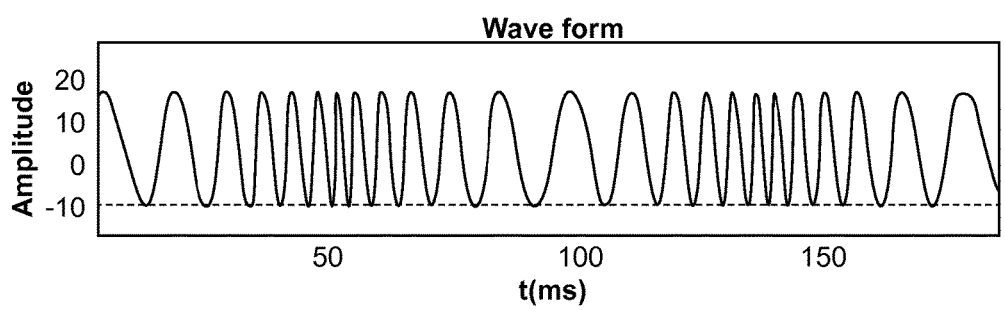
FIG. 6b is a timing diagram of a vibrational waveform measured by the IPG of FIG. 4 when the frequency of the magnetic gradient field generated by the MRI system of FIG. 3 is varied.
Figure 6C:
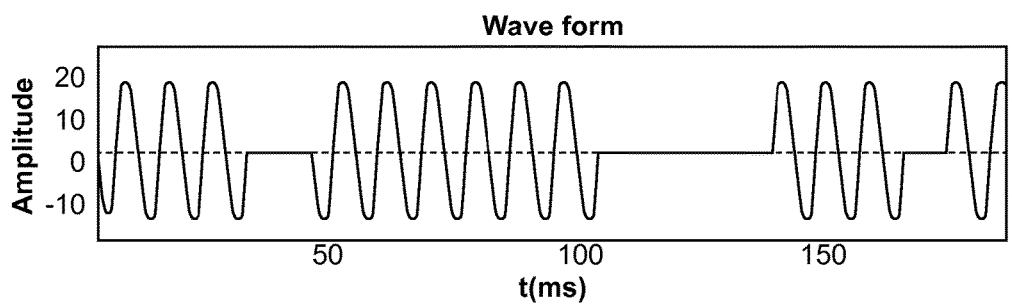
FIG. 6c is a timing diagram of a vibrational waveform measured by the IPG of FIG. 4 when the duty cycle of the magnetic gradient field generated by MRI system of FIG. 3 is varied.

In detecting and measuring the vibrational characteristic(s) of the component(s), the sensing devices 78 reveal the signature in the magnetic gradient field. For example, as shown in waveform of FIG. 6a, the magnitude of the mechanical vibrations changes with time, ostensibly mirroring a change of magnitude in the magnetic gradient field, as mandated by the signature of the magnetic gradient field. Similarly, as shown in the waveform of FIG. 6b, the frequency of the mechanical vibrations changes with time, ostensibly mirroring a change of frequency in the magnetic gradient field, as mandated by the signature of the magnetic gradient field. And, as shown in the waveform of FIG. 6c, the duty cycle of the mechanical vibrations changes with time, ostensibly mirroring a change in the duty cycle of the magnetic gradient field, as mandated by the signature of the magnetic gradient field. It should be appreciated that the x-axis and the y-axis of the plots of FIGS. 6a-6c respectively represent the magnitude of the vibrations (either in units of acceleration, strain, displacement, capacitance, etc.) and time.

In one embodiment, the sensing device 78 may measure a common vibrational characteristic for the component(s) of the IPG 14. For example, the sensing device 78 may be placed only on one component of the IPG 14, and thus, the common vibrational characteristic will simply be the vibrational characteristic measured at the one component of the IPG 14. In another example, sensing devices 78 may be placed on multiple components of the IPG 14, and the common vibrational characteristic will be a function of the vibrational characteristics measured at the multiple components (e.g., averaging the vibrational characteristics of all the components, etc.).

In another embodiment, the sensing device may measure a differential vibrational characteristic of the component(s) of the IPG 14. In one embodiment, sensing devices 78 may be placed on two components of the IPG 14, and the differential vibrational characteristic may refer to a difference in the vibrational characteristics of the two components of the IPG 14. In another embodiment, sensing devices 78 may be placed on two surfaces of the same component, and the differential vibrational characteristic may refer to a difference in the vibrational characteristics of the two surfaces of the same component of the IPG 14. This embodiment may be particularly useful when measuring torsional vibrations. For example, the differential vibrational characteristic(s) can be measured at various locations near an edge of a vibrating conductive surface larger than the common mode components of vibration by a predetermined factor, e.g., a factor of three.

The sensing devices 78 may detect and measure the vibrational characteristic(s) of the mechanical vibrations by measuring an acceleration of the component(s) (e.g., measured in gravity units, i.e., g), measuring a displacement of the component(s) (e.g., measured in μm) and/or measuring a strain on the component(s)(e.g. measured in mm/mm or microstrain (με)). In an alternate embodiment, the sensing devices 78 may detect and measure the vibrational characteristic(s) of the mechanical vibrations by measuring a capacitance of the component(s) (e.g., measured in μF). Acceleration of the component(s) may be measured by using an accelerometer. Displacement of the component(s) may be measured using an accelerometer with a known mass. Strain on the component(s) may be measured using the piezoelectric sensor or a strain gauge. Capacitance may be measured by using a capacitive sensor. In some cases, integrated MEMs systems (in the form of MEMs accelerometers, MEMs piezoelectric sensors, MEMs strain sensors, etc.) may be used to measure acceleration, displacement and/or strain on the component(s). The sensing devices 78 may detect the vibrational characteristic(s) in multiple dimensions (e.g., in the case of measuring acceleration, by using single-axis accelerometers, bi-axial accelerometers and/or tri-axial accelerometers).

The vibrational characteristic(s) detected by the sensing devices 78 are analyzed to identify the signature of the magnetic gradient field. Two ways of analyzing the vibrational characteristic(s) will be discussed. In one embodiment, the signature is identified by a matching an actual pattern of the vibrational characteristic(s) with a known pattern of the vibrational characteristic(s) of the component(s) when exposed to a magnetic gradient field with a signature. In another embodiment, the signature is identified when the actual vibrational characteristic(s) reaches a threshold level the vibrational characteristic(s) is known to reach when exposed to a magnetic gradient field with a signature. The analysis and identification of the signature of the magnetic gradient field will be described in further detail below.

To analyze and identify the vibrational characteristic(s) detected by the sensing devices 78, the microcontroller 66 may run a signature-identification program. The signature-identification program may be based on empirical evidence collected for the mechanical vibrations of the component(s) of the IPG 14. The signature identification program may analyze the vibrational characteristic(s) in either a time-domain or a frequency-domain.

Figure 7A:
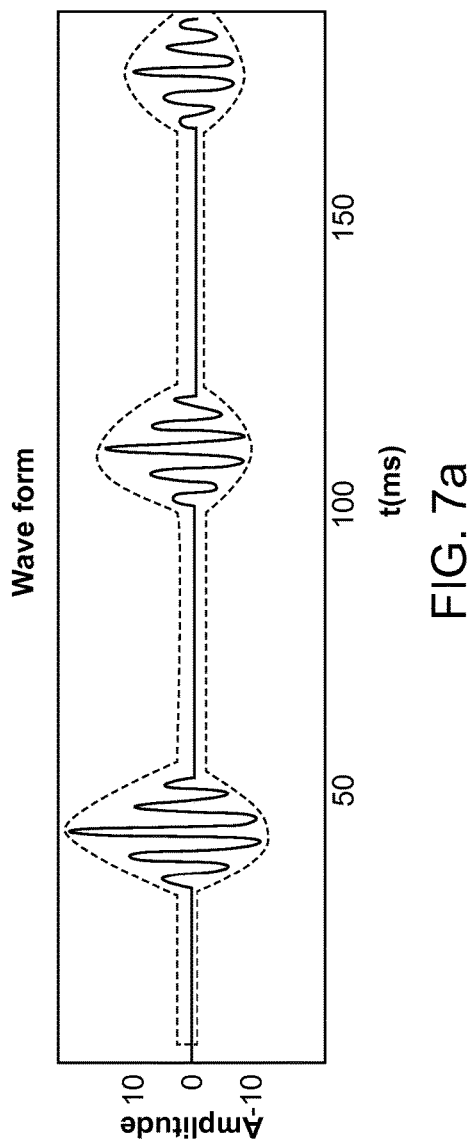
FIG. 7a is a timing diagram of the vibrational waveform of FIG. 6a compared by the IPG of FIG. 4 against a pattern of a pattern matching algorithm.
Figure 7B:
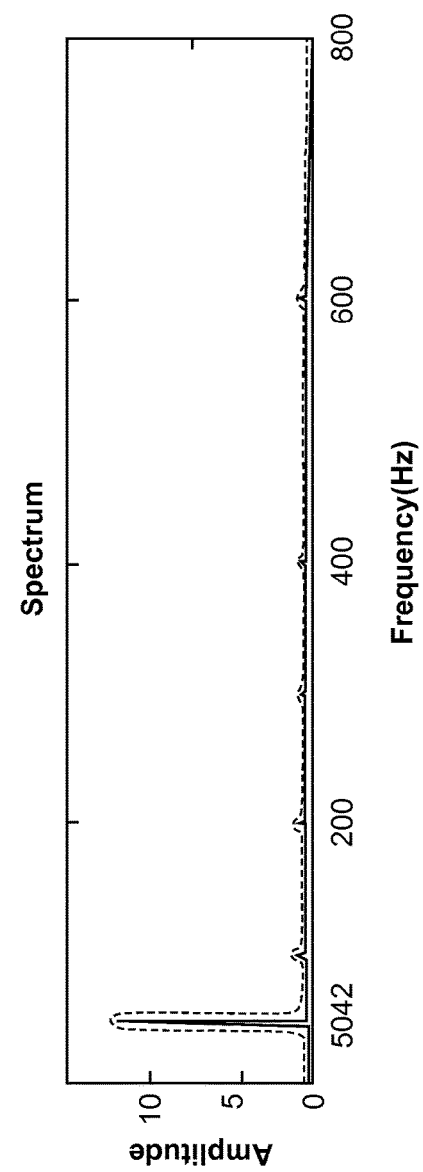
FIG. 7b is a spectral diagram of the vibrational frequencies derived by the IPG of FIG. 4 from the vibrational waveform of FIG. 6a and compared against a pattern of a pattern matching algorithm.

In one embodiment, the signature-identification program may run a pattern-matching algorithm to identify a signature of the magnetic gradient field. The pattern-matching algorithm attempts to match the actual pattern of the vibrational characteristic with a known pattern of the vibrational characteristic associated with a signature. When the two patterns match, the signature of the magnetic gradient field is identified. For example, in FIG. 7a, the pattern of the vibrational characteristic over time fulfills a known pattern (as signified by the dotted line) of the vibrational characteristic associated with a signature. Based on matching patterns, the signature-identification program may then recognize the signature of the magnetic gradient field that caused the mechanical vibrations in the component(s). Similarly, in FIG. 7b (transformed from time-domain to frequency domain), the pattern of the vibrational characteristic fulfills a known pattern (as signified by the dotted line) of the vibrational characteristic, based on which the signature of the magnetic gradient field is identified.

Figure 8A:
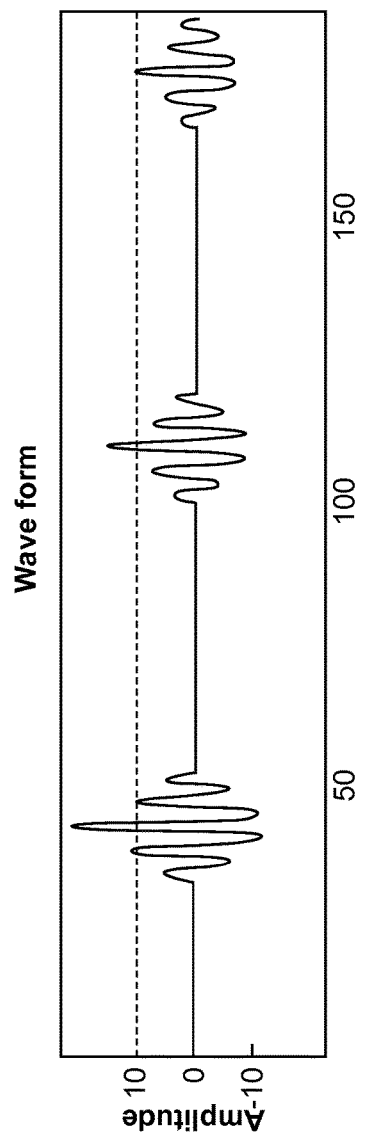
FIG. 8a is a timing diagram of the vibrational waveform of FIG. 6a compared by the IPG of FIG. 4 against a threshold value.
Figure 8B:
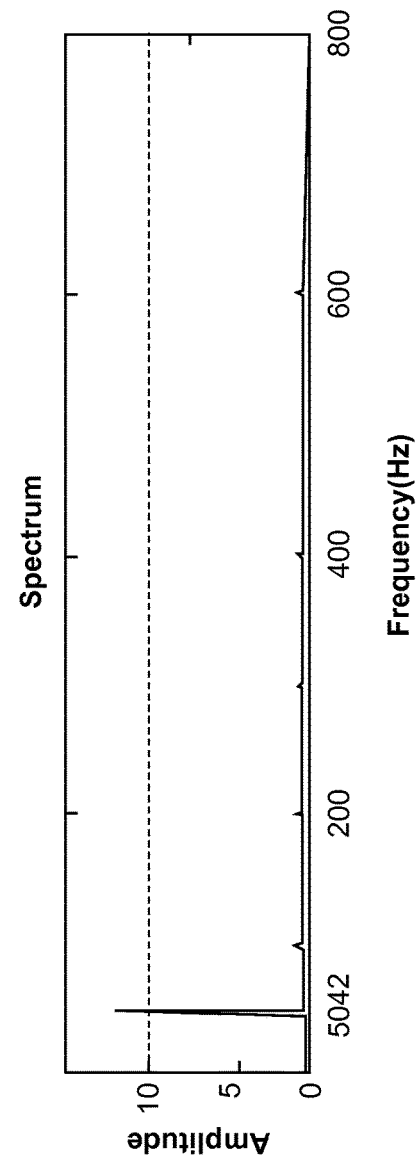
FIG. 8b is a spectral diagram of the vibrational frequencies derived by the IPG of FIG. 4 from the vibrational waveform of FIG. 6a and compared against a threshold value.

In another embodiment, the signature-identification program sets a threshold for the vibrational characteristic to identify a signature of the magnetic gradient field. When the threshold is fulfilled by the actual vibrational characteristic, the signature-identification program identifies the signature of the magnetic gradient field. For example, in FIG. 8a (which is analyzed in time-domain), the threshold (as signified by the dotted line) is fulfilled a prerequisite number of times over a predefined period of time by the vibrational characteristic such that the signature identification program automatically identifies the signature of the magnetic gradient field. Similarly, in FIG. 8b (which is analyzed in frequency-domain), the threshold (as signified by the dotted line) is fulfilled by the vibrational characteristic such that the signature-identification program automatically identifies the signature of the magnetic gradient field.

Figure 9:
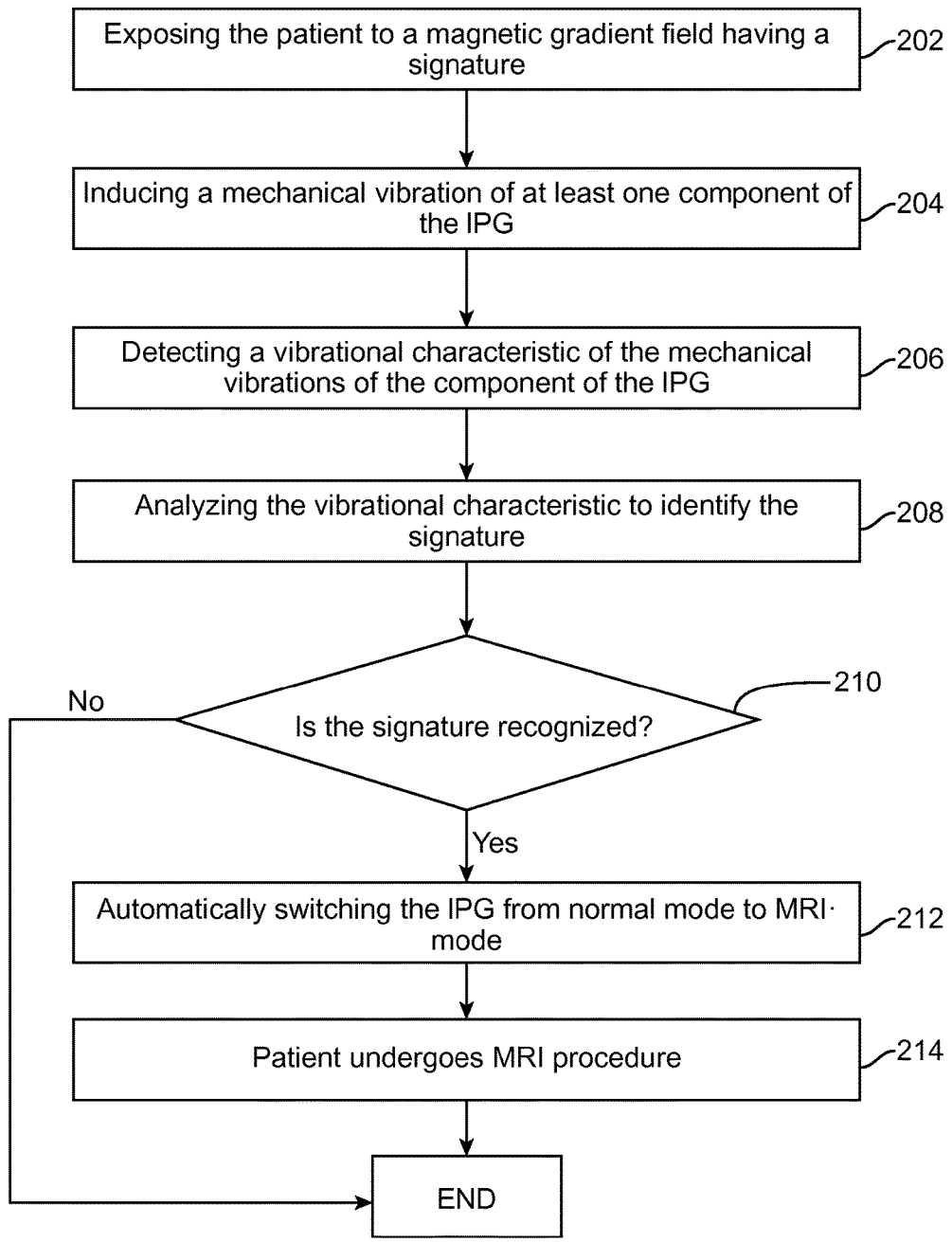
FIG. 9 is a flow diagram illustrating a technique used by the SCM system of FIG. 1 to automatically switch from a normal mode to an MRI-specific mode when a signature of the magnetic gradient field is identified.

Having described the structure and function of the SCM system 10 in the context of MRI procedures, one exemplary technique for switching the IPG 14 from the normal mode to the MRI-specific mode prior to the patient undergoing an MRI procedure will be described with respect to FIG. 9.

The implanted IPG 14, which is currently in a normal mode, is first exposed to a magnetic gradient field having a signature associated with the MRI pre-scan performed by the MRI system 42 (step 202). When the IPG 14 is exposed to the magnetic gradient field having the signature, mechanical vibrations are induced in at least one component of the IPG 14 (step 204). The sensing devices 78 that are coupled to the component(s) of the IPG 14 detect vibrational characteristic(s) of the mechanical vibrations (step 206). The microcontroller 66 executes the signature identification program to analyze the vibrational characteristic(s) (step 208) and to identify the signature of the magnetic gradient field based on the analysis (step 210). If the signature of the magnetic gradient field is identified, the microcontroller 66 automatically switches the IPG 14 into the MRI mode (step 212). The patient then undergoes the MRI procedure with the IPG 14 in MRI-specific mode (step 214). If the signature of the magnetic gradient field is not identified, the IPG 14 remains in normal mode. Thus, the IPG 14 eliminates false positives, and only switches into MRI-specific mode when the signature related to the MRI pre-scan is identified.

Figure 10:
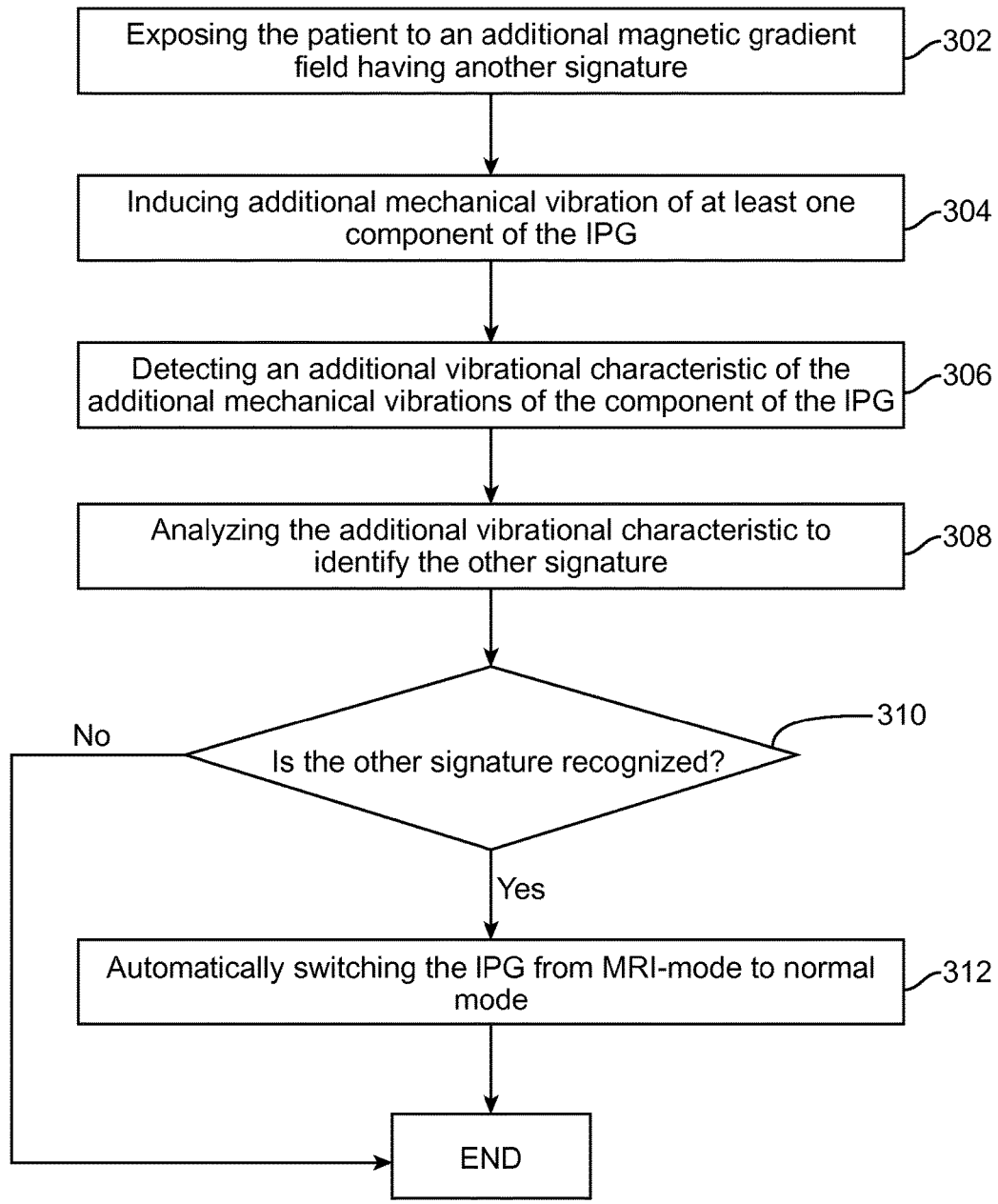
FIG. 10 is a flow diagram illustrating a technique used by the SCM system of FIG. 1 to automatically switch to from the MRI-specific mode to the normal mode when another signature of an additional magnetic gradient field is identified.

Once the MRI procedure is completed, it is desirable that the IPG 14 be switched from the MRI-specific mode to the normal mode in order to resume therapeutic treatment of the patient. To this end, an exemplary technique for switching the IPG 14 from the MRI-specific mode back to the normal mode will be described with respect to FIG. 10.

The implanted IPG 14, which is now in MRI-specific mode, is exposed to an additional magnetic gradient having another signature associated with the MRI post-scan performed by the MRI system 42 (step 302). When the IPG 14 is exposed to the additional magnetic gradient field having the other signature, additional mechanical vibrations are induced in at least one component of the IPG 14 (step 304). The sensing devices 78 that are coupled to the component(s) of the IPG 14 detect additional vibrational characteristic(s) of the additional mechanical vibrations (step 306). The microcontroller 66 executes the signature identification program to analyze the additional vibrational characteristics (step 308), and to identify the other signature of the additional magnetic gradient field based on the analysis (step 310). If the other signature of the additional magnetic gradient field is identified, the microcontroller 66 automatically switches the IPG 14 into the normal mode from the MRI-specific mode (step 312). If the other signature of the additional magnetic gradient field is not identified, the IPG 14 remains in MRI-specific mode.

Although the afore-mentioned technique has been described in the context of an MRI, it should be appreciated that this technique can be used to monitor magnetic fields generated by any source while preventing deactivation of any implantable medical device by the magnetic field.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of automatically identifying a predetermined signature in a time-varying magnetic field generated by a magnetic resonance imaging (MRI) device, comprising:
   exposing a patient to the magnetic field, thereby inducing mechanical vibrations in at least one component of a medical device implanted in the patient;
   executing a programmed, predetermined variation of the time-varying magnetic field generated by the MRI device to produce the predetermined signature in the induced mechanical vibrations in the at least one component;
   detecting a vibrational characteristic of the mechanical vibrations induced in the at least one component;
   analyzing the vibrational characteristic; and
   identifying the predetermined signature of the magnetic field based on the analyzed vibrational characteristic.

2. The method of claim 1, further comprising automatically switching the medical device from a first operational mode to a second operational mode when the predetermined signature is identified.

3. The method of claim 2, further comprising performing an MRI scan on the patient when the medical device is in the second operational mode, thereby generating an MRI of the patient.

4. The method of claim 3, wherein the first operational mode is a fully operational mode, and the second operational mode is an MRI-specific mode.

5. The method of claim 2, further comprising performing an MRI prescan on the patient during which the patient is exposed to the magnetic field.

6. The method of claim 2, further comprising:
   exposing the patient to an additional programmed, predetermined variation in the time-varying magnetic field having another predetermined signature, thereby inducing additional mechanical vibrations in the at least one component;
   detecting an additional vibrational characteristic of the additional induced mechanical vibrations in the at least one component;
   analyzing the additional vibrational characteristic; identifying the other predetermined signature of the magnetic field based on the analyzed other vibrational characteristic; and
   automatically switching the medical device from the second operational mode to the first operational mode when the other predetermined signature is identified.

7. The method of claim 6, further comprising performing an MRI postscan on the patient during which the patient is exposed to the additional magnetic field.

8. The method of claim 6, wherein the predetermined signatures are different from each other.

9. The method of claim 2, further comprising automatically switching the medical device from the second operational mode to the first operational mode when a predetermined period has elapsed.

10. The method of claim 1, wherein the medical device is an implantable pulse generator, and wherein the magnetic field has an amplitude that does not cause the implantable pulse generator to inadvertently stimulate the patient in a harmful manner.

11. The method of claim 1, wherein the predetermined signature is a predetermined pattern in the magnetic field, the analysis of the vibrational characteristic comprises identifying a pattern in the vibrational characteristic corresponding to the predetermined pattern in the magnetic field.

12. The method of claim 1, wherein the analysis of the vibration characteristic comprises thresholding the vibrational characteristic.

13. The method of claim 1, wherein the predetermined signature is a variance in a magnitude of the magnetic field, and the vibrational characteristic is a magnitude of the induced mechanical vibrations.

14. The method of claim 1, wherein the predetermined signature is a variance in a frequency of the magnetic field, and the vibrational characteristic is a frequency of the induced mechanical vibrations.

15. The method of claim 1, wherein the predetermined signature is a variance in a duty cycle of the magnetic field, and the vibrational characteristic is a duty cycle of the induced mechanical vibrations.

16. The method of claim 1, wherein the vibrational characteristic is analyzed in a time-domain.

17. The method of claim 1, wherein the vibrational characteristic is analyzed in a frequency-domain.

18. The method of claim 1, wherein the vibrational characteristic is a common characteristic of the at least one component.

19. The method of claim 1, wherein the vibrational characteristic is a differential characteristic of the at least one component.

20. The method of claim 19, wherein the at least one component is a single component, and the differential vibrational characteristic is detected between at least two different surfaces of the single component.

21. The method of claim 19, wherein the at least one component comprises a first component and a second component, and the differential vibrational characteristic is detected between the first and second components.

22. The method of claim 21, wherein the first and second components comprises a case or a printed circuit board of the medical device and a battery of the medical device.

23. The method of claim 1, wherein the mechanical vibrations are linear in nature.

24. The method of claim 1, wherein the mechanical vibrations are torsional in nature.

25. The method of claim 1, wherein the vibrational characteristic is detected by measuring a vibrational acceleration of the at least one component.

26. The method of claim 1, wherein the vibrational characteristic is detected by measuring a vibrational strain of the at least one component.

27. The method of claim 1, wherein the vibrational characteristic is detected by measuring a vibrational displacement of the at least one component.

28. The method of claim 1, wherein the vibrational characteristic is detected in multiple dimensions.

* * * * *